United States Patent [19]

Weuthen

[11] Patent Number: 5,442,046
[45] Date of Patent: Aug. 15, 1995

[54] ALKYL AND/OR ALKENYL OLIGOGLYCOSIDE ISETHIONATES

[75] Inventor: Manfred Weuthen, Solingen, Germany

[73] Assignee: Henkel Kommanditgesellschaft auf Aktien, Duesseldorf, Germany

[21] Appl. No.: 240,713

[22] PCT Filed: Oct. 30, 1992

[86] PCT No.: PCT/EP92/02500

§ 371 Date: May 9, 1994

§ 102(e) Date: May 9, 1994

[87] PCT Pub. No.: WO93/09125

PCT Pub. Date: May 13, 1993

[30] Foreign Application Priority Data

Nov. 8, 1991 [DE] Germany .................. 41 36 783.9

[51] Int. Cl.$^6$ .............................................. C08B 37/00
[52] U.S. Cl. ................... 536/4.1; 536/18.5; 536/118; 536/120; 536/122; 536/124
[58] Field of Search ............... 536/4.1, 18.5, 118, 536/120, 122, 124

[56] References Cited

U.S. PATENT DOCUMENTS 2,580,352 12/1951 Grassie ............................ 536/92
4,990,609 2/1991 Herzog ............................ 536/92

FOREIGN PATENT DOCUMENTS 0301298 2/1989 European Pat. Off. .
0362671 4/1990 European Pat. Off. .
3291295 12/1991 Japan .

OTHER PUBLICATIONS chemical Abstracts, vol. 116, No. 23, Jun. 8, 1992, Columbus, Ohio, Abstract No. 236083u (Document Unavailable—see Japan 03/291295 above).
Parf. Kosm., 42, 203 (1961).
Bull. Chem. Soc. Jap.,43, 2236 (1970).

Primary Examiner—Douglas W. Robinson
Assistant Examiner—Kathleen Kahler Fonda
Attorney, Agent, or Firm—Wayne C. Jaeschke; John E. Drach; Henry E. Millson, Jr.

[57] ABSTRACT

This invention relates to alkyl and/or alkenyl oligoglycoside isethionates prepared by reacting salts of vinyl sulfonic acid at an elevated temperature and in the presence of basic compounds, with alkyl and/or alkenyl oligoglycosides of the formula (1): $R^1O$—$(G)_p$ in which $R^1$ is a straight-chain or branched-chain aliphatic hydrocarbon group with 6 to 22 carbon atoms and 0, 1,2 or 3 double bonds, G is a glycose unit with 5 or 6 carbon atoms, and p is a number between 1 and 10. The products exhibit marked surface-active characteristics and are useful as surfactants.

19 Claims, No Drawings

ALKYL AND/OR ALKENYL OLIGOGLYCOSIDE ISETHIONATES

BACKGROUND OF THE INVENTION

1. Field of the Invention

This invention relates to alkyl and/or alkenyl oligoglycoside isethionates obtainable by reaction of alkyl and/or alkenyl oligoglycosides with vinyl sulfonates in the presence of basic compounds, to a process for their production and to their use in surface-active preparations.

2. Statement of Related Art

Isethionates are anionic surfactants containing an $-O-CH_2CH_2-SO_3^-$ group which, by virtue of their favorable dermatological compatibility, may be used with advantage in cosmetic preparations (Parr. Kosm., 42, 203 (1961)). They are usually produced from fatty acids or fatty acid esters by condensation with sodium isethionate, propane or butanesultone (Bull. Chem. Soc. Jap., 43, 2236 (1970)).

Unfortunately, the disadvantage of isethionic acid salts and sultones is that their handling involves strict safety requirements and that the products may contain small quantities of these substances as impurities which is undesirable from the toxicological point of view. In addition, known isethionates are not alkali-stable and can contain fatty acids as hydrolysis products which has an adverse effect on their performance properties.

Accordingly, the problem addressed by the present invention was to develop new isethionates which would be free from the disadvantages mentioned above.

DESCRIPTION OF THE INVENTION

This invention relates to alkyl and/or alkenyl oligoglycoside isethionates which are obtained by reaction of alkyl and/or alkenyl oligoglycosides corresponding to formula (I):

$$R^1O-(G)_p \qquad (I)$$

in which
$R^1$ is an aliphatic, linear or branched hydrocarbon radical containing 6 to 22 carbon atoms and 0, 1, 2 or 3 double bonds,
[G] is a glycose unit containing 5 or 6 carbon atoms and
p is an integer of 1 to 10, with salts of vinyl sulfonic acid at elevated temperature in the presence of basic compounds.

It has surprisingly been found that alkyl and/or alkenyl oligoglycosides can be reacted with vinyl sulfonates in the presence of basic catalysts to form compounds having an isethionate structure. The products show unexpectedly good dermatological compatibility, excellent detergent properties, high alkali stability and are readily biodegradable.

Alkyl oligoglycoside isethionates having particularly favorable performance properties are obtained when alkyl oligoglycosides corresponding to formula (I), in which $R^1$ is a $C_{12-18}$ alkyl radical, G is a glucose unit and/or p is a number of 1.1 to 3.0, are used as the starting material.

The present invention also relates to a process for the production of alkyl and/or alkenyl oligoglycoside isethionates which is characterized in that alkyl and/or alkenyl oligoglycosides corresponding to formula (I):

$$R^1O-[G]_p \qquad (I)$$

in which
$R^1$ is an aliphatic, linear or branched hydrocarbon radical containing 6 to 22 carbon atoms and 0, 1, 2 or 3 double bonds,
(G) is a glycose unit containing 5 or 6 carbon atoms and is an integer of 1 to 10, are reacted with salts of vinyl sulfonic acid at elevated temperature in the presence of basic compounds.

Alkyl and/or alkenyl glycosides are known compounds which may be obtained by the relevant methods of preparative organic chemistry. They may be produced from monosugars or polysugars, such as for example glucose or starch, which are acetalized with fatty alcohols in the presence of acidic catalysts either directly or via the intermediate stage of lower alkyl and/or alkenyl glycosides. European patent applications EP 0 301 298 A1 and EP 0 362 671 A1 are cited as representative of the extensive literature available on this subject.

Alkyl and/or alkenyl glycosides (I) in which the glycose unit (G) is derived from aldoses or ketoses are used as starting materials for the production of the alkyl and/or alkenyl glycoside isethionates according to the invention. The reducing saccharides, the aldoses, are preferably used by virtue of their better reactivity. Among the aldoses, glucose is particularly suitable because it is easy to obtain and commercially available. Accordingly, the alkyl and/or alkenyl glycosides particularly preferred as starting materials are the alkyl and/or alkenyl glucosides.

The index p in general formula (I) indicates the degree of oligomerization, i.e. the distribution of monoglycosides and oligoglycosides, and stands for a number of 1 to 10. Whereas p in a given compound must always be an integer and, above all, may assume a value of 1 to 6, the value p for a certain alkyl glycoside is an analytically determined calculated quantity which is generally a broken number. Alkyl and/or alkenyl glycosides having an average degree of oligomerization p of 1.1 to 3.0 are preferably used. Alkyl and/or alkenyl glycosides with a degree of oligomerization of less than 1.7 and, more particularly, between 1.2 and 1.4 are particularly preferred.

The alkyl radical $R^1$ may be derived from primary alcohols containing 6 to 22 and preferably 12 to 18 carbon atoms. Typical examples are caproic alcohol, caprylic alcohol, capric alcohol, lauryl alcohol, myristyl alcohol, cetyl alcohol, palmitoleyl alcohol, stearyl alcohol, oleyl alcohol, elaidyl alcohol, petroselinyl alcohol, linolyl alcohol, linolenyl alcohol, arachyl alcohol, gadolyl alcohol, behenyl alcohol, erucyl alcohol and technical mixtures thereof based on natural fats and oils, for example palm oil, palm kernel oil, coconut oil or beef tallow.

It is preferred to use alkyl oligoglycosides corresponding to formula (I) in which $R^1$ is a $C_{12-18}$ alkyl radical, (G) is a glucose unit and/or p is a number of 1.1 to 3.0.

In the context of the invention, salts of vinyl sulfonic acid are understood to be the alkali metal and/or alkaline earth metal salts of ethylene sulfonic acid ($CH_2=CH-SO_3H$). Typical examples are the lithium, potassium, calcium and magnesium salts of vinyl sulfonic acid. The sodium salt of vinyl sulfonic acid is preferably used.

The molar ratio of alkyl and/or alkenyl oligoglycoside to vinyl sulfonic acid salt may be from 1:5 to 10:1, depending on the number of free hydroxyl groups present in the alkyl and/or alkenyl oligoglycosides. It has proved to be optimal both from the economic point of view and with regard to the properties of the isethionates to use the reactants in a molar ratio of 3:1 to 1:2.

Basic compounds in the context of the invention are understood to be the oxides, hydroxides, carbonates and/or $C_{1-4}$ alcoholates of the alkali and/or alkaline earth metals. Typical examples are lithium hydroxide, sodium hydroxide, potassium hydroxide, calcium oxide, calcium hydroxide, magnesium oxide, magnesium hydroxide, sodium carbonate, magnesium carbonate, sodium methylate, sodium ethylate and potassium tert.butylate. Potassium carbonate is preferably used.

The basic compounds may be used in quantities of 0.1 to 10% by weight and preferably in quantities of 0.5 to 1.5% by weight, based on the alkyl and/or alkenyl oligoglycosides.

Elevated temperatures of 50° to 200° C. are necessary for carrying out the reaction between the alkyl and/or alkenyl oligoglycosides and the vinyl sulfonates.

In one particular embodiment of the process according to the invention, the reactants may be reacted with one another in bulk, i.e. in the absence of water. In this case, reaction temperatures above the melting point of the alkyl and/or alkenyl glycosides of at least 120° C. are necessary. In another embodiment, the glycosides and the vinyl sulfonates may be reacted in aqueous solution. The reaction may be carried out under much milder conditions of 50° to 95° C. In both cases, the reaction time is between 1 and 24 h and preferably between 5 and 12 h and is critically determined by the concentration of catalyst.

The reaction between alkyl and/or alkenyl oligoglycosides and vinyl sulfonates takes place between a hydroxyl group of the glycoside and the double bond of the vinyl sulfonic acid salt. Depending on the amount of vinyl sulfonate used, both monoethers and oligoethers of the glycoside can be formed, accumulating in the form of a statistical mixture.

Alkyl and/or alkenyl oligoglycoside isethionates show excellent detergent properties and, accordingly, are suitable for use in surface-active preparations.

Accordingly, the present invention also relates to the use of alkyl and/or alkenyl oligoglycoside isethionates for the production of laundry detergents, dishwashing detergents and cleaning products and also hair-care and personal hygiene preparations in which they may be present in quantities of 0.1 to 25% by weight and preferably in quantities of 1 to 10% by weight, based on the particular preparation.

The following Examples are intended to illustrate the invention without limiting it in any way.

EXAMPLES

Example 1

250 g (1 mole) of lauryl oligoglucoside (hydroxyl value 656, average degree of oligomerization 1.3; a product of Henkel KGaA, Düsseldorf, FRG) and 2.8 g (0.02 mole) of potassium carbonate were introduced into a 500 ml three-necked flask equipped with a stirrer, internal thermometer and dropping funnel and heated to 160° C. 30 g (0.23 mole) of vinyl sulfonic acid sodium salt were then added to the mixture in portions over a period of 1 h, the reaction temperature gradually being increased to 190° C. After another 3 h, the reaction was terminated, the solid reaction product was size-reduced and dispersed in water.

Example 2

170 g (0.7 mole) of lauryl oligoglucoside from Example 1 and 4.5 g (0.03 mole) of potassium carbonate were introduced into a 500 ml three-necked flask equipped with a stirrer, internal thermometer and dropping funnel and dissolved in approximately 50 ml of water at a temperature of 90° C. 26 g (0.2 mole) of vinyl sulfonic acid sodium salt in the form of a 30% by weight aqueous solution were added to the reaction mixture in portions over a period of 1 h, followed by stirring for another 8 h.

What is claimed is:

1. An alkyl or alkenyl oligoglycoside isethionate which is the product of the reaction of a) at least one salt of vinyl sulfonic acid and b) at least one oligoglycoside selected from the group consisting of alkyl and alkenyl oligoglycosides of the formula $$R^1O(G)_p$$

wherein $R^1$ is an aliphatic, linear or branched hydrocarbon group having from about 6 to about 22 carbon atoms and 0, 1, 2 or 3 double bonds; (G) is a glycose unit having 5 or 6 carbon atoms: and p is a number from 1 to 10, in the presence of a basic catalyst.

2. The product of claim 1 wherein $R^1$ is an alkyl group having from about 12 to about 18 carbon atoms.

3. The product of claim 1 wherein (G) is a glucose unit.

4. The product of claim 1 wherein p has a value of from 1.1 to 3.0.

5. A process for making an alkyl or alkenyl oligoglycoside isethionate which comprises reacting a) at least one salt of vinyl sulfonic acid and b) at least one oligoglycoside selected from the group consisting of alkyl and alkenyl oligoglycosides of the formula $$R^1O(G)_p$$

wherein $R^1$ is an aliphatic, linear or branched hydrocarbon group having from about 6 to about 22 carbon atoms and 0, 1, 2 or 3 double bonds; (G) is a glycose unit having 5 or 6 carbon atoms; and p is a number from 1 to 10, in the presence of a basic catalyst; wherein the reactants are reacted together in the absence of solvents.

6. The process of claim 5 wherein $R^1$ is a $C_{12-18}$ alkyl group.

7. The process of claim 5 wherein (G) is a glucose unit.

8. The process of claim 5 wherein p has a value of from 1.1 to 3.0.

9. The product of claim 1 wherein the molar ratio of alkyl or alkenyl oligoglycoside to vinyl sulfonic acid salt is from about 1:5 to about 10:1.

10. The product of claim 5 wherein the basic catalyst is an alkali metal oxide, alkali metal hydroxide, alkali metal carbonate, alkali metal $C_{1-4}$ alcoholate, alkaline earth metal oxide, alkaline earth metal hydroxide, alkaline earth metal carbonate, alkaline earth metal $C_{1-4}$ alcoholate, or a combination thereof.

11. The process of claim 5 wherein the amount of basic catalyst is from about 0.1% to about 10% by weight of alkyl or alkenyl oligoglycoside.

12. The product of claim 1 wherein the at least one salt of viny sulfonic acid is selected from the group consisting of alkali metal and alkaline earth metal salts.

13. The product of claim 1 wherein p has a value of from 1.2 to 1.4.

14. The product of claim 1 wherein the molar ratio of alkyl or alkenyl oligoglycoside to vinyl sulfonic acid salt is from about 3:1 to about 1:2.

15. The process of claim 5 wherein the reaction is carried out at a temperature in the range of from about 120° to about 200° C.

16. The product of claim 1 wherein $R^1$ is an alkyl group having from 12 to 18 carbon atoms, (G) is a glucose unit, p has a value of from 1.1 to 3.0; the molar ratio of alkyl or alkenyl oligoglycoside to vinyl sulfonic acid salt is from about 1:5 to about 10:1; and the at least one salt of vinyl sulfonic acid is selected from the group consisting of alkali metal and alkaline earth metal salts.

17. In a laundry detergent, dishwashing detergent, cleaning product, hair-care preparation or personal hygiene preparation, the improvement wherein from about 0.1 to about 25% by weight of the product of claim 1 is present therein.

18. The composition of claim 17 wherein from about 1 to about 10% of the product of claim 1 is present therein.

19. In a laundry detergent, dishwashing detergent, cleaning product, hair-care preparation or personal hygiene preparation, the improvement wherein from about 0.1 to about 25% by weight of the product of claim 16 is present therein.

* * * * *